United States Patent
Kerschbaumer

(10) Patent No.: US 8,542,360 B2
(45) Date of Patent: Sep. 24, 2013

(54) METHOD AND APPARATUS FOR PRODUCING A NEW SHADE GUIDE HAVING NEW COLOR VALUES FROM KNOWN COLOR ELEMENTS

(75) Inventor: Harald Kerschbaumer, Klaus (AT)

(73) Assignee: Ivoclar Vivadent AG, Schaan (LI)

( * ) Notice: Subject to any disclaimer, the term of this patent is extended or adjusted under 35 U.S.C. 154(b) by 723 days.

(21) Appl. No.: 12/217,796

(22) Filed: Jul. 9, 2008

(65) Prior Publication Data

US 2009/0033927 A1    Feb. 5, 2009

(30) Foreign Application Priority Data

Jul. 30, 2007    (DE) .......................... 10 2007 035 610

(51) Int. Cl.
*A61C 19/10*    (2006.01)
*G01J 3/50*    (2006.01)

(52) U.S. Cl.
CPC  *A61C 19/10* (2013.01); *G01J 3/508* (2013.01)
USPC ............................................ 356/421; 433/26

(58) Field of Classification Search
USPC .......................................... 356/421; 433/26
See application file for complete search history.

(56) References Cited

U.S. PATENT DOCUMENTS

| | | | |
|---|---|---|---|
| 5,653,589 A | | 8/1997 | Kleinmann |
| 5,725,372 A | * | 3/1998 | Leon ................................. 433/26 |
| 6,139,318 A | | 10/2000 | Foser |
| 7,118,374 B2 | | 10/2006 | Culp |
| 2003/0156283 A1 | * | 8/2003 | Jung et al. ...................... 356/326 |
| 2004/0252303 A1 | * | 12/2004 | Giorgianni et al. ............ 356/402 |

OTHER PUBLICATIONS

VIDENT.COM—VITA 3-D Master Shade Guide—from the Internet p. 1 of 1 printed Jul. 9, 2008.
DENTEXPO.ORG—page showing Ivoclar Chromascop Universal Guide, VITAPAN classic, & VITAPAN 3d Master shade guides—from the internet p. 1 of 2—printed Jul. 9, 2008.

* cited by examiner

*Primary Examiner* — Michael A Lyons
*Assistant Examiner* — Rebecca C Bryant
(74) *Attorney, Agent, or Firm* — Hodgson Russ LLP

(57) ABSTRACT

The invention relates to a method (100) for producing color elements of a shade guide. To this end, color values of known color elements (15) of shade guides (10) with similar lightness values, hues and chromata are initially ascertained. In another method step, the color values of each new color element are determined while increasing a color distance (16) between the lightness values, hues and chromata of the previously ascertained color values.

13 Claims, 1 Drawing Sheet

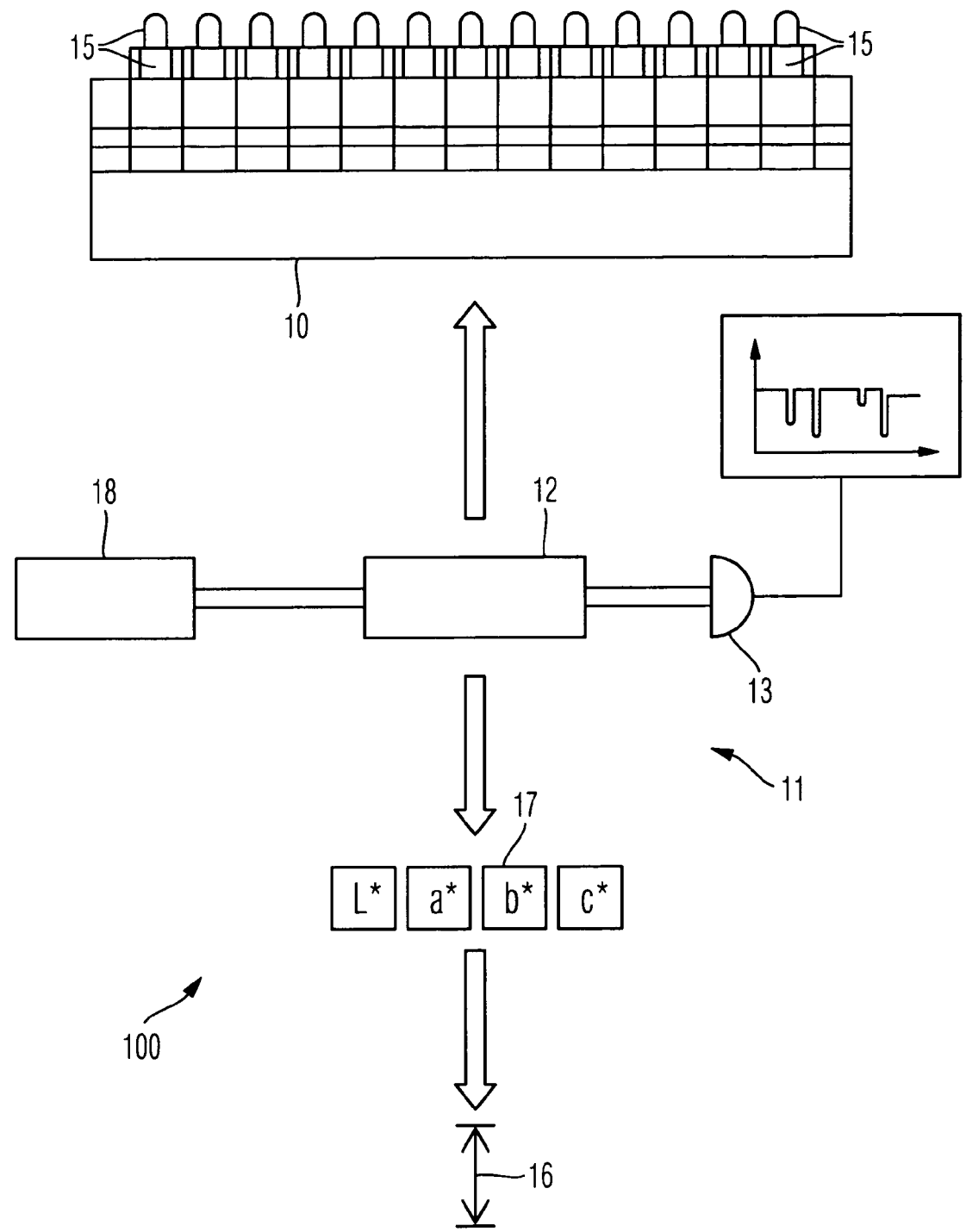

METHOD AND APPARATUS FOR PRODUCING A NEW SHADE GUIDE HAVING NEW COLOR VALUES FROM KNOWN COLOR ELEMENTS

CROSS-REFERENCE TO RELATED APPLICATIONS

This application claims foreign priority benefits under 35 U.S.C. §119(a)-(d) from German patent application ser. no. P 10 2007 035 610.4 filed Jul. 30, 2007.

TECHNICAL FIELD

The invention relates to a method for producing individual color elements of a shade guide by ascertaining color values of known color elements of shade guides with similar lightness values, hues and chromata, and determining new color values for new color elements while increasing a color distance between the lightness values and/or hues and/or chromata of the ascertained color values; and to the corresponding shade guide having a plurality of individual color elements.

BACKGROUND OF THE INVENTION

In the field of tooth replacement, the color composition of artificial teeth is becoming more and more important. Corresponding to the different color compositions of natural teeth, manufacturers and suppliers of tooth replacement find it necessary to offer a large number of possible colors. A color range of less than 20 different colors currently represents a minimum number for meeting the demands of patients.

As aid for choosing the color of artificial teeth, so-called shade guides are used. Such shade guides comprise a body with a plurality of insertion pockets, into which color selection pins can be inserted. These color selection pins are in turn provided with color tabs attached at one end, whose color corresponds in particular to the artificial tooth. The color selection pins (or color pins) further have a handle which can be inserted into an insertion pocket.

The color selection pins can then be composed depending on the discretion of the dental technician or dentist in any desired manner. It is also already known to design shade guides in a modular fashion. To this end, according to a certain hue, similar colors are supported in a common carrier in combined form on the shade guide.

In the field of tooth replacement, the shade guides "Vitapan classic" and "Vita 3D-Master" from Vita AG are also used. Both of these shade guides contain several color groups which differ from one another with respect to their colors (reddish, yellowish, brownish and grayish). Within these color groups, color samples differ in turn with respect to their lightness.

Another shade guide used for the color composition of artificial teeth is called "chromascop" and contains 20 different color samples. Together with the shade guide "Vitapan classic", which has 16 different color samples, it is already possible to fabricate artificial teeth, such as incisors, lateral teeth and molars, in 36 different colors.

Most recently, however, customers have articulated requests to produce artificial teeth according to the Color samples of the "Vita 3D-Master". Thus, approximately 20% of dentists in the USA currently determine the tooth colors using the "Vita 3D-Master".

This leads to the problem, however, of using the new shade guides together with the already existing shade guides with the result that another 26 new colors corresponding to the colors of the "Vita 3D-Master" have to be developed and fabricated. This would mean the fabrication and storage of artificial teeth in 62 different colors, which would incur not inconsiderable costs and involve a confusing pattern in the shade guides.

OBJECTS AND SUMMARY OF THE INVENTION

Proceeding from the represented disadvantages and citing the disclosed prior art in methods of the type mentioned in the introduction, the present invention is therefore based on the object of developing a method of the type mentioned in the introduction such that the three previously mentioned shade guides can be reproduced without the need to use the already mentioned shade guide yet also not to make available a large number of further colors for further shade guides.

The method according to the invention includes the steps of firstly ascertaining color values of known color elements of the shade guides with similar lightness values, hues and chromata. Then, color values of each new color element are determined while increasing a color distance between the lightness values, hues and chromata of the previously ascertained color value.

The invention is based on the realization that it is advantageous to combine those colors from the color groups of all three shade guides which are substantially identical, and also to effect approximations in an optimized manner in order to allow a selection which is at least not worse despite the reduction in the color value number—with respect to the sum of the color value numbers of the three shade guides. Surprisingly, increasing the color distances between the lightness values, hues and chromata—and thus a lower number of individual color elements—still enables an improved selection and also facilitates the selection for the dental technician or dentist.

In order to obtain an accurate general idea of the similarity of colors of the individual shade guides, i.e. the shade guides "chromascop", "Vitapan classic" and "Vita 3D-Master", the lightnesses, hues and chromata are ascertained by means of spectroscopic tests. Using the measured spectroscopic data, the teeth are sorted within the framework of the invention to form groups which exhibit the greatest similarities first in terms of lightness (L*), hue (a* or b*) and chroma (c*)

In the case of similar colors, it is possible to refer to hardly distinguishable color differences, if the color distance, i.e. the so-called dimensionless delta E value, is below a unit of 0.7. Deviations up to a value of delta E 1.5 can be seen only by the trained eye. The values are here given without dimensions. It is, however, also possible to use as dimensional types for the lightness, the hue, the chroma and the color distance all the dimensional types known for this purpose.

If the delta E values cover the above mentioned range, and there is also a correspondence in a visual comparison, these very similar colors can be combined into one color.

This is illustrated once again using the following example:

|    | color 1      | color 2      | color 3     | common color |
|----|--------------|--------------|-------------|--------------|
| L* | 75.10/DL 0.4 | 75.5/DL 0    | 74.5/DL 1   | 75.5         |
| a* | 1.02/Da 0.08 | 0.72/Da 0.38 | 1.4/Da −0.3 | 1.1          |
| b* | 19.30/Db −0.4| 19.40/Db −0.5| 18.1/nb 0.8 | 18.9         |
| De | 0.57         | 0.62         | 1.3         |              |

-continued

| color 1 | color 2 | color 3 | common color |
|---------|---------|---------|--------------|

DL = Delta L* value, the difference between the L* value of the color 1 and the L* value of the common color.
Da = Delta a* value, the difference between the a* value of the color 1 and the a* value of the common color.
Db = Delta b* value, the difference between the b* value of the color I and the b* value of the common color.
De = Delta E value is the sum of delta L* a* b*.

In this way it is possible for a new color to replace all three colors without any losses in terms of quality. It is also scarcely possible to detect a color difference visually.

For larger color differences, the procedure may be as follows:

The colors are arranged staggered according to chroma; i.e. the less chromatic colors are located at the start, then follow the colors with a higher chroma.

| color | opaque | dentine |
|-------|--------|---------|
| 1 | A | A |
| 2 | B | A |
| 3 | B | B |
| 4 | c | B |
| 5 | c | c |

For color 1, in each case one opaque (A) and one dentine (A) are colored, for color 2, which is of course somewhat more intensive, an associated opaque (B) is used and the dentine (A) of the color 1. The exact hue for color 2 can be controlled via the opaque. The same opaque (B) as for the color 2 is used for the color 3, the higher chroma is achieved via an associated dentine (B). The series can be continued like this ad infinitum.

In addition, the invention provides a shade guide with a plurality of individual color elements which form the basis for the production of artificial teeth. To this end, the color values of color systems or shade guides, which are known per Se, are ascertained with respect to their lightness values and/or hues and/or chromata, with the color values of each then new individual color element, based on the color values thus ascertained, being determined for increasing the color distance between the lightness values, hues and chromata.

In another advantageous embodiment, provision is made for the lightness, hues and chromata of the known color elements to be ascertained by means of spectroscopic tests.

In another advantageous embodiment, provision is made for the color values with similar lightness values to be ascertained from the shade guides Chromascop and/or Vitapan classic and/or Vita 3D-Master.

In another advantageous embodiment, provision is made for at least one opaque color and/or at least one dentine color, which are colored identically or differently, to be colored for the new color values.

In another advantageous embodiment, provision is made for the known color elements to be divided into groups with different lightness, within which the difference between the lightness of each known color element and the average lightness of each lightness group is 0.5 to 2.5, in particular 0.5 to 1.5.

In another advantageous embodiment, provision is made for the known color elements within each lightness group to be divided into color groups, within which the difference between the color and/or the chroma of each known color element and the average color and/or the average chroma of each color group is 0.5 to 2, in particular 0.5 to 1.

In another advantageous embodiment, provision is made for the color of each new color element within the color range to have similar distances with respect to the further colors within each color group.

In another advantageous embodiment, provision is made for the new shade guide to be divided into 5 to 9, in particular 7, lightness groups.

In another advantageous embodiment, provision is made for the shade guide to have at least three different color elements within each lightness group.

In another advantageous embodiment, provision is made for the color elements to be detachably attached to a base body of the shade guide.

In another advantageous embodiment, provision is made for the color elements to be fabricated at least partially from dental material.

In another advantageous embodiment, provision is made for each color element to be provided with a marking and/or designation.

BRIEF DESCRIPTION OF THE FIGURES

Further advantages, details and features of the invention ensue from the following description of the exemplary embodiment of the invention using the drawing in which:

FIG. 1 shows a schematic representation of the method according to the invention.

DETAILED DESCRIPTION

The method 100 represented schematically in FIG. 1 is used to produce individual color elements of a shade guide.

The method 100 begins with the ascertaining of color values of color elements 1~ of known shade guides 10 with similar lightness values, hues and chromata. The shade guides 10 are the shade guides "Chromascop", "Vitapan Classic" and "Vita 3D-Master".

In order to obtain a general idea of similarities among the color values of the color elements 15 of the individual shade guides 10, the lightnesses, hues and chromata of the color values are measured using a spectrometer 11 which is suitable therefor and can have a radiation source 18, the sample 12 with the color value of the color 14 and a detector 13.

These data are used to sort the teeth into groups 17, which exhibit the greatest similarities first in terms of lightness (L*), hue (a* and b*) and chroma (c*)

In a subsequent step, the color values of each individual color element 15 are determined while increasing the color distance 16 between the lightness values, hues and chromata. An increase in the color distance 16 implies in this case a smaller number of color elements.

Within the context of the invention, the color differences are hardly distinguishable if the color distance 16 is less than a unit of 0.7, with it also being possible for the conventionally used units to be used rather than this dimensionless unit. Deviations up to a value of the color distance 16 of 1.5 are also only visible to the trained eye.

If within the context of the method according to the invention the values of the color differences lie within this range, the very similar colors can be grouped together into one color.

Color distances 16 which lie under a unit of 1.0 or 2.0 are ascertained. The lightness values and the chromata differ at most by the unit 1.5, whereas the difference in the case of the hues is at most 1.0.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method for producing color elements of a new shade guide comprising the following method steps:
   a) ascertaining color values of lightness values, hues, and chroma of a plurality of known color elements of two or more existing shade guides with similar lightness values, hues, and chroma via a spectrometer;
   b) grouping the known color elements from the two or more existing shade guides into groups with different lightness, within which the difference "delta E" between the lightness of each known color element and the average lightness of each lightness group is 0.5 to 2.5; and
   b) determining a plurality of new color values for new color elements for a new shade guide while increasing a color distance between the lightness values and/or hues and/or chroma from the grouped color elements, the plurality of new color elements being within the "delta E" of the corresponding grouped color elements;
   wherein the plurality of new color elements of the new shade guide is less than the plurality of color elements of the two or more existing shade guides.

2. The method as claimed in claim 1, wherein the two or more existing shade guides (10) are Chromascop and/or Vitapan classic and/or Vita 3D-Master.

3. The method as claimed in claim 1, wherein the color distance between each of the new color elements is approximately equal.

4. A new shade guide system, comprising:
   a plurality of color elements for the production of artificial teeth, the plurality of color elements having color values being within a "delta E" of grouped existing color elements from two or more existing shade guides, the grouped existing color elements corresponding to color elements from the two or more existing shade guides within which the "delta E" between the lightness of each color element and the average lightness of each lightness group is 0.5 to 2.5;
   wherein the plurality of color elements for the production of artificial teeth is less than the color elements of the two or more existing shade guides.

5. The shade guide as claimed-in claim 4, wherein the new shade guide is divided into 5 to 9 lightness groups.

6. The shade guide its claimed in claim 5, wherein the shade guide has at least three different color elements within each lightness group.

7. The shade guide as claimed in claim 6, wherein the color elements are detachably attached to a base body of the shade guide.

8. The shade guide as claimed in claim 6, wherein the color elements are fabricated at least partially from dental material.

9. The shade guide as claimed in claim 6, wherein each color element is provided with a marking and/or designation.

10. The method as claimed in claim 1, wherein the difference "delta E" between the lightness of each existing color element (15) and the average lightness of each lightness group is 0.5 to 1.5.

11. The method as claimed in claim 1, wherein at least one opaque color and/or at least one dentine color, which are colored identically or differently, are colored for the color values.

12. The method as claimed in claim 1, wherein the known color elements (15) within each lightness group are divided into color groups, within which the difference between the color and/or the chroma of each existing color element (15) and the average color and/or the average chroma of each color group is 0.5 to 2.

13. The shade guide as claimed in claim 4, wherein the difference "delta E" between the lightness of each existing color element (15) and the average lightness of each lightness group is 0.5 to 1.5.

* * * * *